United States Patent
Satake et al.

(10) Patent No.: US 8,876,292 B2
(45) Date of Patent: Nov. 4, 2014

(54) FUNDUS IMAGING APPARATUS (75) Inventors: Norimasa Satake, Nukata (JP);
Yukihiro Higuchi, Toyota (JP)

(73) Assignee: Nidek Co., Ltd., Gamagori (JP)

(*) Notice: Subject to any disclaimer, the term of this patent is extended or adjusted under 35 U.S.C. 154(b) by 199 days.

(21) Appl. No.: 13/541,465

(22) Filed: Jul. 3, 2012

(65) Prior Publication Data

US 2014/0009738 A1  Jan. 9, 2014

(51) Int. Cl.
*A61B 3/14* (2006.01)
*A61B 3/10* (2006.01)

(52) U.S. Cl.
CPC .. *A61B 3/102* (2013.01); *A61B 3/14* (2013.01)
USPC .............................. 351/206; 351/210; 351/221

(58) Field of Classification Search
CPC ........ A61B 3/10; A61B 3/102; A61B 3/1025; A61B 3/14; A61B 3/15
USPC ........................... 351/205, 206, 210, 211, 221
See application file for complete search history.

(56) References Cited

U.S. PATENT DOCUMENTS 7,301,644 B2   11/2007  Knighton et al.
7,589,842 B2   9/2009   Kuroiwa
7,824,035 B2   11/2010  Yamada et al.
8,534,835 B2 * 9/2013   Murata et al. .................. 351/206
2013/0107277 A1 * 5/2013  Hirose et al. ................... 356/512

FOREIGN PATENT DOCUMENTS

JP   2009-291252 A   1/2009

* cited by examiner

*Primary Examiner* — Huy K Mai
(74) *Attorney, Agent, or Firm* — Stetina Brunda Garred & Brucker (57) ABSTRACT A fundus imaging apparatus includes: an interference optical system configured to detect, with a detector, an interference state between a reference light and a measurement light that is reflected at a fundus; an optical scanner configured to scan the fundus with the measurement light; an optical member configured to adjust an optical path length difference between the measurement light and the reference light; an imaging unit configured to photograph a tomographic image of the fundus based on an output signal from the detector; a first optical path length adjuster configured to move the optical member, based on a light-receiving signal output from the detector corresponding to a position of the optical member; a second optical path length adjuster configured to readjust a position of the optical member; and an optical system adjuster configured to adjust the interference optical system between adjustments by the first and second optical path length adjusters.

18 Claims, 7 Drawing Sheets

SCANNING LINE

FIG. 5

S
SCANNING LINE
P1
VARIATION OF
LUMINANCE DISTRIBUTION

FUNDUS IMAGING APPARATUS

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present disclosure relates to a fundus imaging apparatus that generates a fundus tomographic image of an examinee's eye.

2. Related Art

An optical tomographic image imaging apparatus that photographs a fundus tomographic image of an examinee's eye includes an optical coherence tomography (OCT) using low coherent light (see JP-A-2009-291252).

With the optical tomographic image photographing apparatus, an examiner adjusts a focus of a fundus tomographic image based on a focus state of a fundus front image obtained by an SLO optical system or a fundus camera optical system. The examiner adjusts an optical path length and a light polarization state (adjustment of a polarizer) after the focus adjustment, thus optimizing measurement.

Recently, a fundus imaging apparatus without a dedicated optical system for photographing fundus front images such as the SLO optical system and the fundus camera optical system has been proposed (see U.S. Pat. No. 7,301,644). This apparatus two-dimensionally scans a fundus with a measurement light flux. A spectral intensity of an interference signal obtained by a light-receiving element at each scanning point is integrated so as to obtain a front image.

BRIEF SUMMARY

A fundus photographing apparatus includes: an interference optical system configured to split light flux emitted from a light source into a measurement light and a reference light, the interference optical system detecting, with a detector, an interference state between the reference light and the measurement light that is reflected at a fundus of an examinee's eye; an optical scanner disposed on an optical path of the measurement light, the optical scanner scanning the fundus with the measurement light; a driver configured to drive an optical member, the optical member being disposed on the optical path of the measurement light or on an optical path of the reference light so as to adjust an optical path length difference between the measurement light and the reference light; a photographing unit configured to photograph a tomographic image of the fundus based on an output signal from the detector; a first optical path length adjuster configured to obtain a light-receiving signal output from the detector corresponding to a position of the optical member while moving the optical member by controlling the driver, the first optical path length adjuster moving the optical member to a position where the fundus tomographic image is obtained, based on the light-receiving signal; a second optical path length adjuster configured to readjust a position of the optical member adjusted by the first optical path length adjuster; and an optical system adjuster configured to adjust the interference optical system between adjustments by the first optical path length adjuster and the second optical path length adjuster.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The apparatus disclosed in U.S. Pat. No. 7,301,644 adjusts a photographing condition without a dedicated optical system for photographing a fundus front image such as an SLO optical system and a fundus camera optical system. The apparatus adjusts a focus, an optical path length, and a light polarization state with an OCT optical system. This makes it difficult to automate the adjustment of the photographing condition compared with the apparatus with the dedicated optical system. This causes the automatic adjustment to end without completion of the adjustment, which leads to an inappropriate display of a fundus tomographic image on a monitor.

Figure 1:
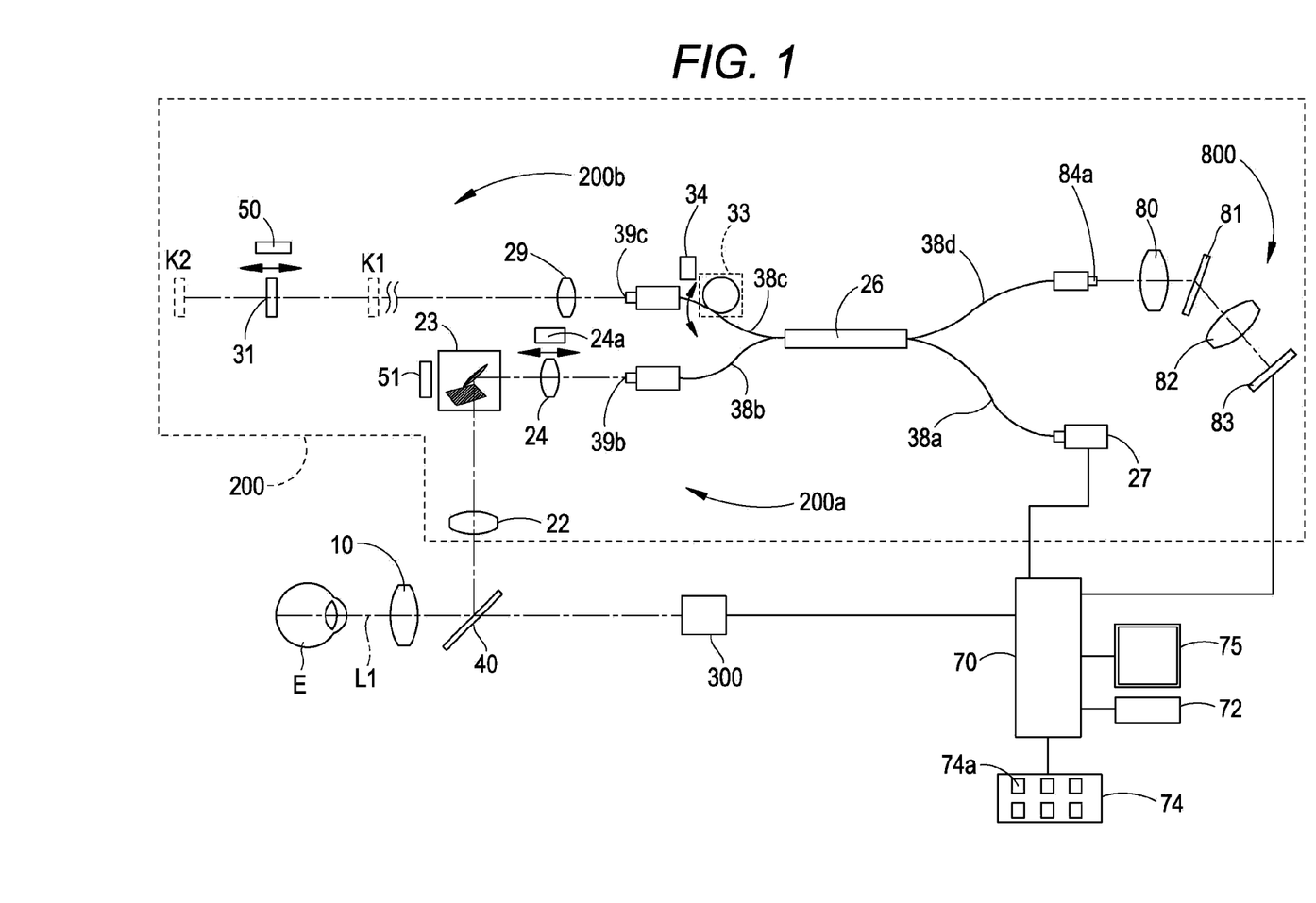
FIG. 1 is a block diagram illustrating an optical system and a control system of an optical tomographic image photographing apparatus according to an embodiment.

A technical problem in the disclosure is to provide a fundus photographing apparatus that appropriately adjusts a photographing condition and then obtains a fundus tomographic image, without the dedicated optical system for photographing a fundus front image. An optical tomographic image photographing apparatus of the present invention (this apparatus) that is a fundus photographing apparatus according to the embodiment will be described by referring to the accompanying drawings. FIG. 1 is a block diagram illustrating an optical system and a control system of the optical tomographic image photographing apparatus. A fundus photographing apparatus is one example of ophthalmic photographing apparatuses. In this embodiment, the depth direction of an examinee's eye is designated as Z-direction (direction of an optical axis L1), the horizontal direction component in the plane perpendicular to the depth direction is designated as X-direction, and the vertical direction component in the plane is designated as Y-direction.

As shown in FIG. 1, the optical system of the apparatus includes an interference optical system 200 (OCT optical system) and a fixation-target projecting unit 300. The interference optical system 200 divides a light flux emitted from a light source into a measurement light and a reference light. Next, the interference optical system 200 guides the measurement light flux to the fundus of an examinee's eye and guides the reference light to a reference light optical system. Then the interference optical system 200 detects an interference state between the reference light and the measurement light reflected at the fundus with a detector. The interference state is an interference state of a resultant light obtained by mixing both of the lights. The interference optical system 200 includes a measuring optical system 200a and a reference light optical system 200b. The interference optical system 200 includes a spectral optical system 800. The spectral optical system 800 disperses the interference light into a spectrum of individual frequencies (wavelengths). The dispersed interference lights are received on a light receiver (one-dimensional light-receiving element 83 in this embodiment). A dichroic mirror 40 has a property that reflects light with approximately the same wavelength component as that of the measurement light of the OCT optical system 200 while transmitting light with approximately the same wavelength component as that of the light used by the fixation-target projecting unit 300.

First, a configuration of the OCT optical system 200 disposed on a reflection side of the dichroic mirror 40 will be described. An OCT light source 27 emits a low coherent light used as the measurement light and the reference light of the OCT optical system 200. The OCT light source 27 employs, for example, a light source (for example, an SLD light source) that emits a light with a center wavelength of 840 nm and a bandwidth of 50 nm. The fiber coupler 26 functions as both of a light splitting member and a light combining member. Light emitted from the OCT light source 27 is divided by the fiber coupler 26 into the reference light and the measurement light through an optical fiber 38a as an optical path. The measurement light is guided to the examinee's eye E through an optical fiber 38b. On the other hand, the reference light is guided to a reference mirror 31 through an optical fiber 38c and a polarizer 33 (polarizing element).

An optical path that guides the measurement light to the examinee's eye E includes an end portion 39b of the optical fiber 38b, a focusing lens 24, a scanning unit 23, and a relay lens 22. The end portion 39b emits the measurement light. The focusing lens 24 (focusing optical member, focus adjuster) is movable in an optical axis direction in order to correct a diopter scale for the fundus of the examinee's eye. The scanning unit 23 includes a combination of two galvanometer mirrors. The scanning unit 23 (optical scanner) is configured to scan the fundus in X-Y direction with the measurement light, and is driven by a scanning driving mechanism 51. The dichroic mirror 40 and an objective lens 10 function as a light guiding optical system that guides an OCT measurement light from the OCT optical system 200 to the fundus of the examinee's eye.

The end portion 39b of the optical fiber 38b emits the measurement light. The measurement light reaches the scanning unit 23 through the focusing lens 24. The two galvanometer mirrors of the scanning unit 23 are driven to change a reflection direction of the measurement light. The measurement light, which is reflected at the scanning unit 23, is reflected at the dichroic mirror 40 through the relay lens 22 and is then condensed on the fundus of the examinee's eye through the objective lens 10.

The measurement light, which is reflected at the fundus, is reflected at the dichroic mirror 40 through the objective lens 10, and then is guided to the OCT optical system 200. Further, the measurement light passes through the relay lens 22, the two galvanometer mirrors of the scanning unit 23, and the focusing lens 24, and then enters the end portion 39b of the optical fiber 38b. The measurement light, which enters the end portion 39b, passes through the optical fiber 38b, the fiber coupler 26, and an optical fiber 38d, and then reaches an end portion 84a of the optical fiber 38d.

Meanwhile, an optical path that guides the reference light to the reference mirror 31 includes the optical fiber 38c with an end portion 39c, which emits the reference light, a collimator lens 29, and the reference mirror 31. A part of the optical fiber 38c constitutes the polarizer 33. That is, the polarizer 33 includes a metal housing and the part of the optical fiber 38c, which is coiled inside the metal housing. A driving mechanism 34 rotates the polarizer 33. This changes a polarization direction (light polarization state) of the reference light.

The polarizer 33 is not limited to this configuration insofar as the polarizer 33 is located in the measurement optical path or the reference optical path, and substantially matches the polarization states of the measurement light and the reference light. The polarizer 33 may be, for example, a polarizer that uses a half wavelength plate or a quarter wavelength plate, or a polarizer that changes a light polarization state by deforming a fiber with pressure.

The polarizer 33 (polarization controller) matches polarization directions of the measurement light and the reference light. In view of this, the polarizer 33 is applicable insofar as the polarizer 33 adjusts at least one of the polarization directions of the measurement light and the reference light. For example, the polarizer 33 may be located on the measurement optical path.

A reference mirror driving mechanism 50 (driver) drives the reference mirror 31 (optical member) located on the optical path of the measurement light or the reference light. This adjusts the optical path length of the measurement light or the reference light. In this embodiment, the reference mirror 31 is located on the optical path of the reference light and movable in the optical axis direction. This allows the reference mirror 31 to vary the optical path length of the reference light.

The end portion 39c of the optical fiber 38c emits the reference light. The reference light is collimated into a parallel light flux by the collimator lens 29 and then reflected at the reference mirror 31. The reflected light is condensed by the collimator lens 29 and then enters the end portion 39c of the optical fiber 38c. The reference light that has entered the end portion 39c reaches the fiber coupler 26 through the optical fiber 38c and the polarizer 33.

As described above, the reference light, which is generated from the light emitted from the light source 27, and a fundus reflection light, which is obtained by reflection of the measurement light at the fundus of the examinee's eye, are combined by the fiber coupler 26, thus providing the interference light. The interference light is emitted from the end portion 84a through the optical fiber 38d.

The spectral optical system 800 (spectrometer unit) disperses the interference light into frequency components in order to obtain an interference signal for each frequency. The spectral optical system 800 includes a collimator lens 80, a grating mirror 81 (diffraction grating), a condenser lens 82, and a light-receiving element 83 (detector). The light-receiving element 83 includes a one-dimensional detector (line sensor) with sensitivity to a light in the infrared wavelength region.

The interference light, which is emitted from the end portion 84a, is collimated into the parallel light by the collimator lens 80, and is then dispersed into frequency components by the grating mirror 81. The dispersed interference light is condensed on a light-receiving surface of the detector 83 (light-receiving element) through the condenser lens 82. Thus, spectral information in the interference fringe is recorded on the light-receiving element 83. Then a controller 70 photographs a tomographic image of the eye based on the output signal from the light-receiving element 83. That is, the spectral information (light-receiving signal) is input from the light-receiving element 83 to the controller 70. The controller 70 (a photographing unit, a first optical path length adjuster, a second optical path length adjuster, an optical system adjuster, a fundus observer, a polarization adjuster, an adjustment determiner, and an adjustment terminating unit) 70 analyzes the spectral information using Fourier transform, thus measuring information of the examinee's eye in the depth direction. The controller 70 uses the scanning unit 23 to scan a fundus with the measurement light in a predetermined traverse direction, thus obtaining a tomographic image. For example, the controller 70 scans the fundus in X direction or Y direction with the measurement light so as to obtain a tomographic image (fundus tomographic image) on X-Z or Y-Z plane of the fundus of the examinee's eye. In this embodiment, a method that obtains a tomographic image by one-dimensionally scanning the fundus with the measurement light is referred to as B-scan. The obtained fundus tomographic image is stored in a memory 72 coupled to the controller 70. Further, the controller 70 may drive the scanning unit 23 to two-dimensionally scan the fundus with the measurement light in X-Y direction. In view of this, the controller 70 may obtain a two-dimensional moving image of a fundus of an examinee's eye in X-Y direction or a three-dimensional image of the fundus of the examinee's eye, based on the output signal from the light-receiving element 83.

The reference mirror 31 is driven by the driving mechanism 50 and is movable in the optical axis direction. A movable range of the reference mirror 31 is set to accommodate for variation in ocular axial lengths of examinees' eyes. As shown in FIG. 1, the reference mirror 31 is movable in a range between a movement limiting position K1 in a direction to shorten the optical path length of the reference light and a movement limiting position K2 in a direction to lengthen the optical path length of the reference light.

The initial position (movement start position) of the reference mirror 31 prior to a start of the automatic optical path length adjustment (first automatic optical path length adjustment, specifically described later) is set at the movement limiting position K1 or the movement limiting position K2. Obviously, the initial position may be a position (midpoint) between the position K1 and the position K2. The initial position may be changeable for convenience.

The focusing lens (focusing optical member) 24 is driven by a driving mechanism 24a and then moved in the optical axis direction. The focusing lens 24 has a movable range between the first movement limiting position and the second movement limiting position. The first movement limiting position is, for example, a position corresponding to a refractive power of −15 D, that is, a position to focus with the refractive power of −15 D. The second movement limiting position is, for example, a position corresponding to a refractive power of +15 D.

The initial position of the focusing lens 24 is a position corresponding to an average eye refractive power of the examinee's eye (for example, a position corresponding to a refractive power of 0 D). Obviously, another position may be the initial position. The initial position may be configured to be changeable. The initial position may be either the first movement limiting position or the second movement limiting position.

The polarizer 33 is driven by the driving mechanism 34 so as to rotate. The polarizer 33 has a rotation range between a first rotation limiting position (for example, 0 degrees) and a second rotation limiting position (for example, 180 degrees).

An angle (rotation position) of the polarizer 33 is set between the first rotation limiting position and the second rotation limiting position. The polarizer 33 does not rotate until the second automatic optical path length adjustment (described later) is completed. Thus, the initial position of the polarizer 33 is a position (midpoint) between both of the limiting positions.

Next, the fixation-target projecting unit 300 will be described. The fixation-target projecting unit 300 includes an optical system to guide a visual line of the eye E. The fixation-target projecting unit 300 includes a fixation target that is presented to the eye E, and is able to guide a direction of visual line of the eye E to a plurality of directions.

For example, the fixation-target projecting unit 300 includes a visible light source that emits visible light, and two-dimensionally changes the target presenting position. In view of this, a change in a direction of visual line results in changing a photographed portion. For example, when the fixation target is presented from the same direction as the photographing optical axis, a center of the fundus is set as the photographed portion. When the fixation target is presented above the photographing optical axis, an upper portion of the fundus is set as the photographed portion. That is, the photographed portion is changed corresponding to the position of the target relative to the photographing optical axis.

The fixation-target projecting unit 300 may employ, for example, a configuration that adjusts the fixation position by adjusting a lighting state of a plurality of LEDs arranged in a matrix, or a configuration that adjusts the fixation position by a combination of scanning with an optical scanner using light of the light source and controlling lighting or non-lighting of the light source. The fixation-target projecting unit 300 may employ an internal fixation light type or an external fixation light type.

The controller 70 is coupled to, for example, a display monitor 75, a memory 72, a control unit 74, the reference mirror driving mechanism 50, the driving mechanism 24a, which moves the focusing lens 24 in the optical axis direction, and the driving mechanism 34.

Figure 2:
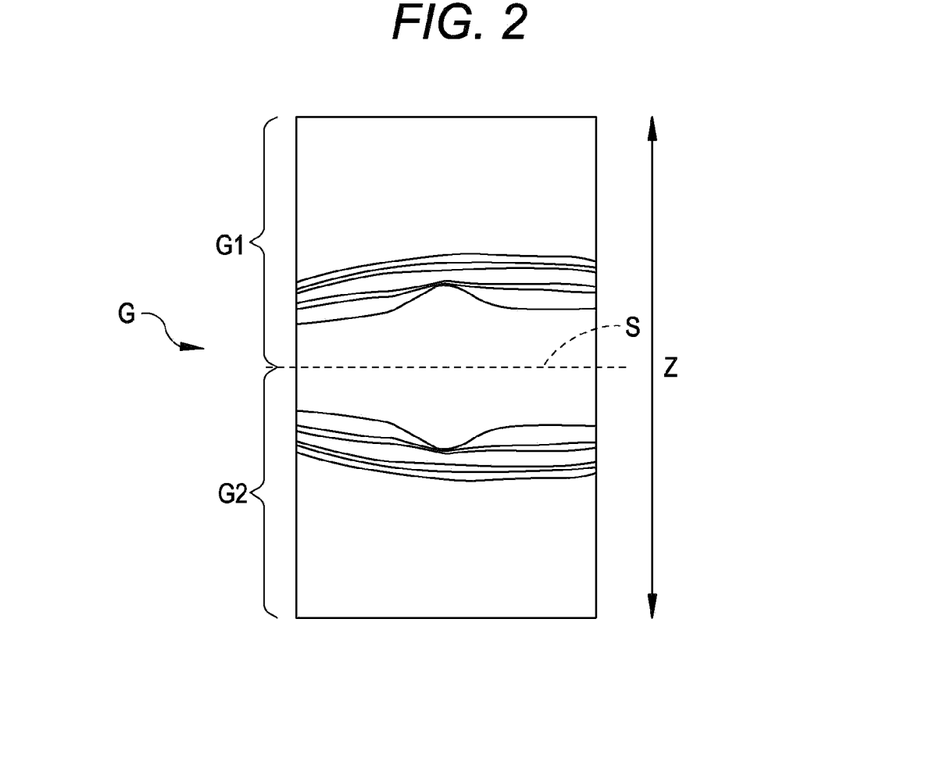
FIG. 2 is a view illustrating an exemplary tomographic image obtained by an OCT optical system.

FIG. 2 is a view illustrating an exemplary tomographic image obtained (formed) by the OCT optical system 200. This apparatus obtains a tomographic image adjacent to a depth position S of the fundus where the optical path lengths of the measurement light and the reference light match. An image range G (photographing ranges) obtained by this apparatus includes a first image range G1 and a second image range G2. The first image range G1 is image data corresponding to a position at the deeper side of the depth position S in the fundus. On the other hand, the second image range G2 is image data corresponding to a position at the shallower side of the depth position S in the fundus. The images of the first image range G1 and the second image range G2 are mutually symmetrical with respect to the depth position S.

In the case where the reference mirror 31 is located such that the depth position S is disposed at the shallower side of the retinal surface, a fundus tomographic image (normal image) where a retinal surface side has a higher sensitivity than a choroidal side is obtained. In this case, the fundus tomographic image obtained from the first image range G1 and the fundus tomographic image obtained from the second image range G2 face one another (in a state where respective portions corresponding to the retina of the both images are adjacent). In this case, a real image is obtained from the first image range G1 while a virtual image (mirror image) is obtained from the second image range G2.

On the other hand, in the case where the reference mirror 31 is located such that the depth position S is disposed at the deeper side of the retinal surface, a fundus tomographic image (inverted image) where the choroidal side has higher a sensitivity than the retinal surface side is obtained. In this case, the fundus tomographic image obtained from the first image range G1 and the fundus tomographic image obtained from the second image range G2 face opposite directions one another (in a state where respective portions corresponding to the chorioid of the both images are adjacent). In this case, a real image is obtained from the second image range G2 while a virtual image (mirror image) is obtained from the first image range G1.

The controller 70 selects, for example, one of the first image range G1 and the second image range G2 as an image range to obtain a real image, and displays the real image on the monitor 75. In this embodiment, the controller 70 is configured to select the first image range G1.

In this embodiment, the controller 70 executes a dispersion correction process with software on spectral information (spectral data) that is output from the light-receiving element 83. The controller 70 obtains a depth profile based on the spectral information after the dispersion correction. In view of this, the real image and the virtual image have different image qualities.

The controller 70 obtains, for example, a first dispersion correction value (for a normal image) as a dispersion correction value for correcting an effect of dispersion on a real image from the memory 72. The controller 70 corrects spectral information output from the light-receiving element 83 using the first dispersion correction value. The controller 70 executes the Fourier transform on the corrected spectral information (spectral intensity data) so as to generate fundus tomographic image data. This makes the real image obtained from the first image range G1 an image with high sensitivity and high resolution. On the other hand, the virtual image obtained from the first image range G1 is a blurred image with low resolution due to a difference of the dispersion correction values.

This should not be construed in a limiting sense. The dispersion correction by software may be executed on the virtual image. The controller 70 may be configured to obtain a real image from the second image range G2. Further, the controller 70 may be configured to obtain a real image from both of the first image range G1 and the second image range G2. The image range to obtain a real image may be conveniently selected by an examiner to operate a given switch.

Figure 3:
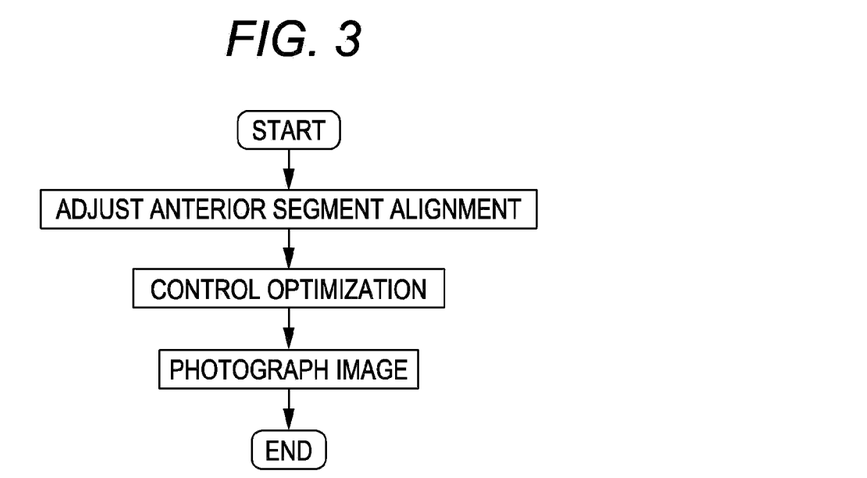
FIG. 3 is an operational flow chart of the optical tomographic image photographing apparatus.

Operations of the apparatus thus configured will be described. FIG. 3 is an operational flow chart of the optical tomographic image photographing apparatus. The examiner instructs the examinee to gaze at a fixation target of the fixation-target projecting unit 300. Then the examiner performs an alignment such that the measurement optical axis is positioned at the pupil center of the examinee's eye using a joystick (not shown) while observing an anterior segment observation image, which is photographed by an anterior segment observation camera (not shown), on the monitor 75.

Next, a photographing condition is optimized so that a fundus portion the examiner desires to observe can be observed with high sensitivity and high resolution. In this embodiment, this optimization includes an optical path length adjustment, a focus adjustment, and an adjustment of the light polarization state (polarizer adjustment).

The examiner presses an optimization starting switch 74a (optimize switch) disposed at the control unit 74. When an operation signal is sent from the optimization starting switch 74a, the controller 70 sends a trigger signal to start optimization, thus starting optimization.

The controller 70 adjusts a focus position between the first optical path length adjustment and the second optical path length adjustment when optimizing a photographing condition. The optimization according to the embodiment is executed, for example, in the order of the first automatic optical path length adjustment, the focus adjustment, the second automatic optical path length adjustment, and the polarizer adjustment. When the examiner presses a photographing switch (not shown) after completion of the optimization, a fundus tomographic image is photographed and stored in the memory 72.

In this embodiment, the first automatic optical path length adjustment, the focus adjustment, and the polarizer adjustment are performed by detecting a signal intensity of the tomographic image. In the following description, a predetermined evaluation value B is employed as an index indicating the signal intensity.

Figure 4:
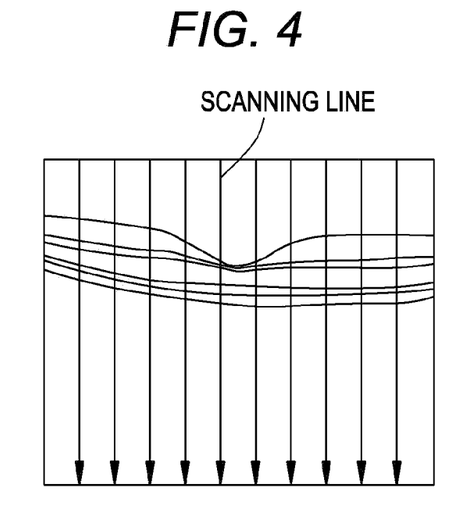
FIG. 4 is a view illustrating scanning lines set to obtain luminance distribution data on the tomographic image.

The evaluation value B is obtained with the following formula: B=((average maximum luminance value of an image)−(average luminance value in a background area of the image))/(standard deviation of the luminance value in the background area). The controller 70 obtains luminance distribution data of the tomographic image based on a light-receiving signal from the light-receiving element 83. FIG. 4 is a view of an image displayed on the screen of the monitor 75 in the case where the reference mirror, the focusing lens, and the polarizer are located in respective predetermined positions.

Figure 5:
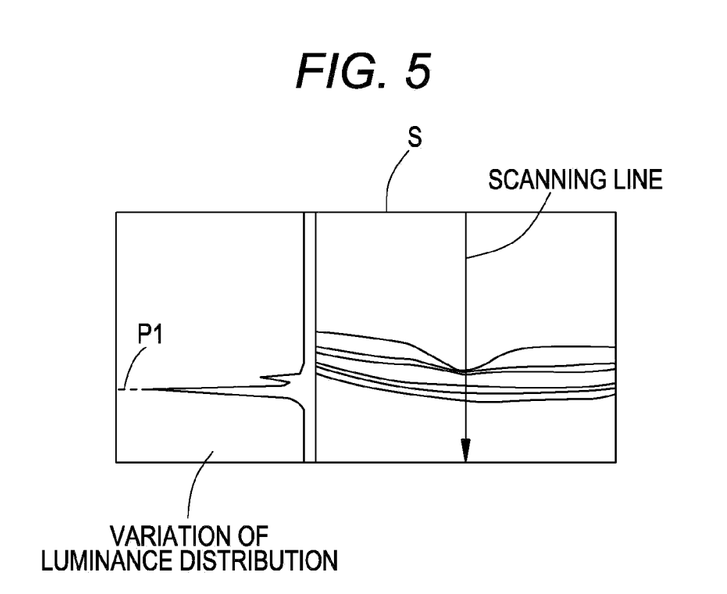
FIG. 5 is a graph illustrating a variation of luminance distribution in a depth direction of an image.

The controller 70 firstly sets a plurality of scanning lines corresponding to a scan in the depth direction (A-scan direction). Further, the controller 70 obtains luminance distribution data on the respective scanning lines. In the example shown in FIG. 4, the scanning lines include ten splitting lines to split an image into ten. FIG. 5 is a graph illustrating a variation of luminance distribution in the depth direction of an image.

Here, the controller 70 calculates luminance values that are maximum (hereinafter referred to as maximum luminance value) from luminance distributions corresponding to the respective scanning lines. The controller 70 calculates the maximum luminance value in the fundus tomographic image as an average value of the maximum luminance values of the respective scanning lines. Then, the controller 70 calculates an average value of the luminance values of the respective scanning lines in the background area as an average luminance value of the fundus tomographic image in the background area.

The evaluation value B thus calculated is used for the first automatic optical path length adjustment, the focus adjustment, and the polarizer adjustment. In this case, it is preferred to use the tomographic image obtained from the first image range G1 in order to calculate the evaluation value B.

(Optimization)

Figure 6:
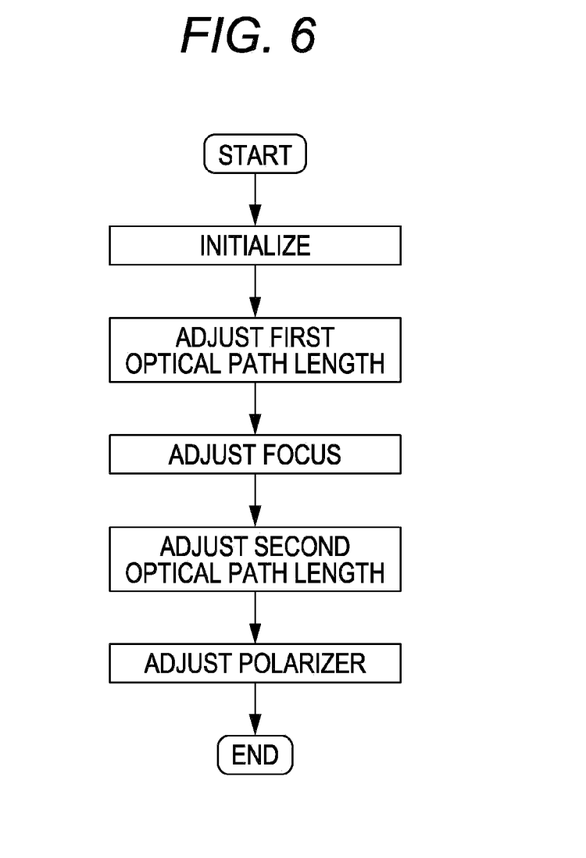
FIG. 6 is an operational flow chart of an optimization according to the embodiment.

FIG. 6 is an operational flow chart of the optimization of a photographing condition according to the embodiment. The controller 70 sets the reference mirror 31 and the focusing lens 24 at the respective initial positions when initializing the apparatus. Then the controller 70 moves the reference mirror 31 from the initial position in one direction by predetermined increments so as to perform the first optical path length adjustment (first automatic optical path length adjustment). After completion of the first optical path length adjustment, the controller 70 obtains focus position information. The controller 70 moves the focusing lens 24 to the focus position based on the focus position information, thus performing an autofocus adjustment. Then after completion of the autofocus adjustment, the controller 70 again moves the reference mirror 31 in the optical axis direction, thus performing an optical path length adjustment (fine optical path length adjustment; the second optical path length adjustment). After completion of the second optical path length adjustment, the controller 70 drives the polarizer 33 so as to adjust the light polarization state of the reference light.

An example of the optimization will be specifically described below.

(Initialization)

First, the controller 70 initializes this apparatus. In this initialization, the controller 70 moves the reference mirror 31 and the focusing lens 24 to respective initial positions (movement start positions).

In the initialization, the controller 70 selects one of the movement limiting position K1 and the movement limiting position K2 as the initial position of the reference mirror 31. In this respect, the controller 70 selects, as the initial position, the movement limiting position closer to the position of the reference mirror 31 before the start of initialization. Then, the controller 70 moves the reference mirror 31 to the selected initial position. Obviously, the initial position and the movement direction of the reference mirror 31 may be determined based on another criterion.

The controller 70 moves the focusing lens 24 to the initial position (position corresponding to 0 D in this embodiment).

(First Automatic Optical Path Length Adjustment (Rough Adjustment))

Figure 7:
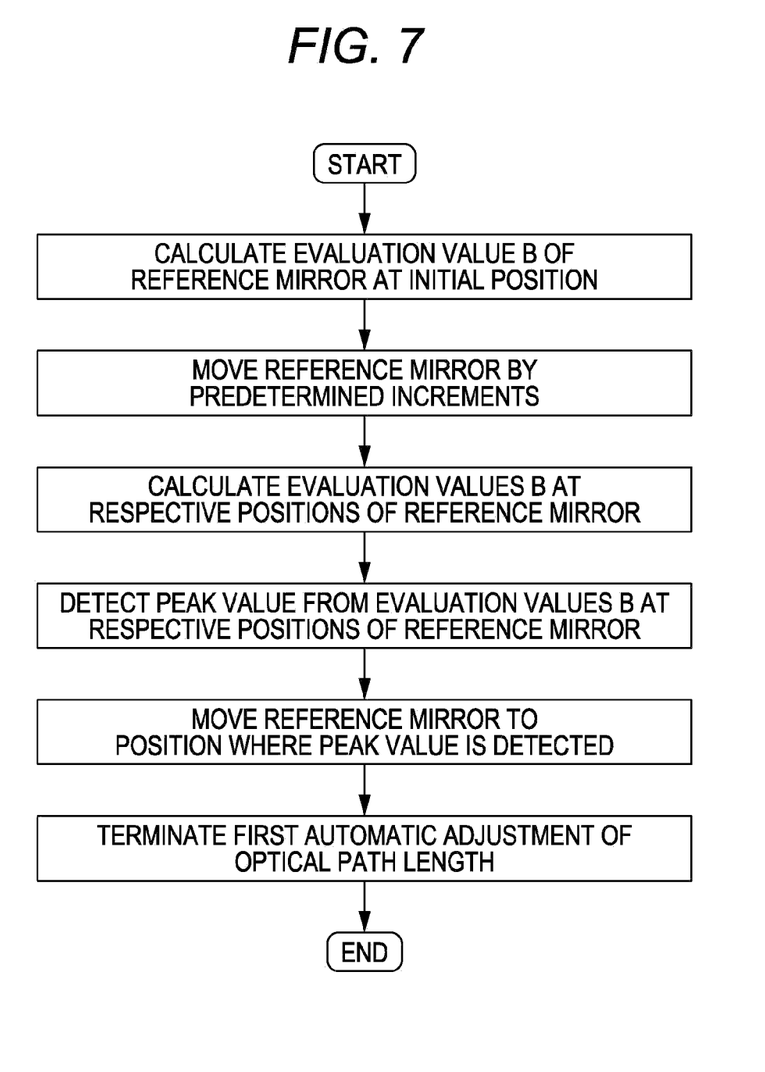
FIG. 7 is an operational flow chart of a first automatic adjustment of an optical path length.

The initialization is completed as described above. Next, the controller 70 executes the first automatic optical path length adjustment (automatic rough optical path length adjustment). FIG. 7 is an operational flow chart of a first automatic adjustment of an optical path length.

The controller 70 controls the driving mechanism 50 so as to move the reference mirror 31. Further, the controller 70 obtains a position of the reference mirror 31 that allows obtaining a fundus tomographic image based on the output signal from the light-receiving element 83 corresponding to the position of the reference mirror 31, thus moving the reference mirror 31 to that position.

Specifically, the controller 70 obtains the tomographic image at this initial position. Then the controller 70 moves the reference mirror 31 to the other different movement limiting position from the initial position. For example, in the case where the limiting position K1 is selected (set) as the initial position of the reference mirror 31, the controller 70 moves the reference mirror 31 to the limiting position K2.

Here, the controller 70 moves the reference mirror 31 by predetermined increment (for example, 2 mm increment as a photographing range), and then sequentially obtains tomographic images at respective moved positions. This allows the controller 70 to search a position of the reference mirror 31 to obtain a fundus tomographic image.

In this case, the controller 70 obtains a tomographic image each time the reference mirror 31 is stopped at the discretely set moved position. Then, the controller 70 analyzes the tomographic images obtained at the respective positions. For example, the controller 70 calculates evaluation values B of the tomographic images obtained at the respective positions. Then, the controller 70 relates positions of the reference mirror 31 to respective evaluation values B of the tomographic image, and stores them in the memory 72.

Figure 8:
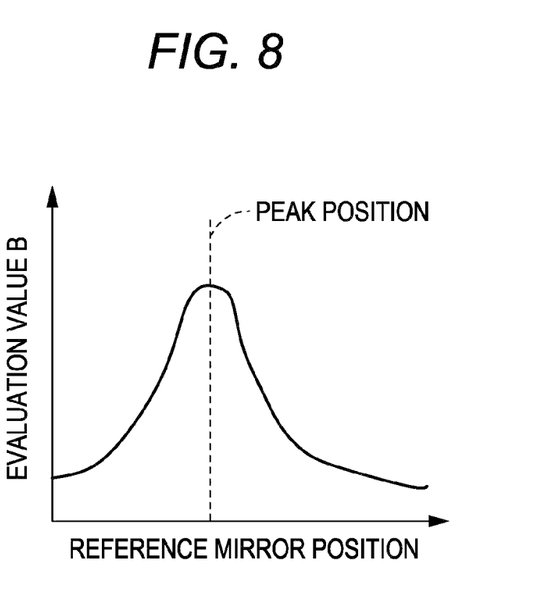
FIG. 8 is a graph illustrating exemplary calculation results of evaluation values of respective positions of a reference mirror.

FIG. 8 is a graph illustrating an exemplary correspondence relation between calculation results of the evaluation values B and respective positions of the reference mirror 31. FIG. 8 shows positions of the reference mirror on the horizontal axis and the evaluation values B at respective positions on the vertical axis.

Here, the controller 70 detects the peak of the evaluation values B based on the calculation results of the evaluation values B corresponding to the positions of the reference mirror 31. Then, the controller 70 stores the position of the reference mirror 31 corresponding to the peak in the memory 72. Then, the controller 70 moves the reference mirror 31 to a position corresponding to the peak of the evaluation values B. Generally, a position of the reference mirror 31 where a real image of the fundus appears in the tomographic image is the position where the peak of the evaluation values B is detected. However, if it is out of focus, the position of the reference mirror 31 where a virtual image appears in the tomographic image may be a position where the peak of the evaluation value B is detected.

As described above, the optical path length is roughly adjusted. This allows to display at least a part of the fundus tomographic image on somewhere on the monitor 75.

When the controller 70 obtains the evaluation values B while moving the reference mirror 31 by predetermined increments, the controller 70 may stop driving of the reference mirror 31 where the evaluation values B stop increasing and start decreasing. The controller 70 may estimate the position of the reference mirror 31 corresponding to the peak, based on the calculation results of the evaluation values B corresponding to the positions of the reference mirror 31. This estimation is executed, for example, by generating an approximated curve of the variation in the evaluation values B.

(Autofocus Adjustment)

The controller 70 executes the focus adjustment after completion of the first automatic optical path length adjustment.

After the first automatic optical path length adjustment, the controller 70 moves the focusing lens 24 to a position to focus (focus position) on the fundus of the examinee's eye, based on the output signal from the light-receiving element 83.

Specifically, the controller 70 drives the driving part 24a (focus adjuster, focus adjusting member) and moves the lens 24 from the predetermined initial position by predetermined increments. Then, the controller 70 sequentially obtains tomographic images corresponding to the moved positions of the lens 24 so as to search the focus position.

For example, the controller 70 moves the lens 24 to the movement limiting position in an increment of 0.5 D. In the case where the focus position is not found, the controller 70 then moves the lens 24 in the opposite direction. The increment to move the lens 24 should not be construed in a limiting sense. The increment may be, for example, 1 D or 2 D. The increment may be conveniently set.

In the search of the focus position, the controller 70 analyzes the image obtained at each position where the controller 70 stops the focusing lens 24 at the discretely set moved position. For example, the controller 70 calculates the evaluation values B of the tomographic image obtained at the respective positions. Then, the controller 70 relates the positions of the lens 24 to the evaluation values B of the tomographic image, and stores them in the memory 72.

Here, the controller 70 detects the peak of the evaluation values B based on the calculation results of the evaluation values B corresponding to the positions of the focusing lens 24. Then, the controller 70 moves the focusing lens 24 to the position corresponding to the peak. The focus adjustment is thus completed.

(Second Optical Path Length Adjustment (Fine Adjustment))

After this focus adjustment, the controller 70 readjusts the position of the reference mirror 31 from the position adjusted by the first automatic optical path length adjustment, based on the output signal from the light-receiving element 83.

Specifically, after completion of the focus adjustment, the controller 70 moves the reference mirror 31 based on the tomographic image obtained by the focus adjustment, thus performing the second automatic optical path length adjustment.

Here, the controller 70 determines whether the fundus tomographic image, which is obtained from the first image range G1 after adjustment of its focus, is a real image or a virtual image. For example, the controller 70 determines that the fundus tomographic image is a real image if a half-value width of the peak of luminance distribution in the depth direction is smaller than a predetermined allowable width. On the other hand, the controller 70 determines that the fundus tomographic image is a virtual image if the half-value width is larger than the predetermined allowable width. It is possible to use any other method insofar as the method uses a difference in image quality between the real image and the virtual image so as to determine whether the tomographic image is a real image or a virtual image. In this determination, in addition to the half-value width, a contrast of the tomographic image and a rising degree of the edge of the tomographic image or the like is available. This determination may use a shape of the fundus tomographic image.

The controller 70 moves the reference mirror 31 in a direction that allows obtaining a real image (direction to shorten the reference optical path) if the fundus tomographic image to be obtained is determined to be a virtual image. At this time, the controller 70 calculates a movement amount of the reference mirror 31 such that a deviation amount between an optical-path-length matching position S and an image detecting position (predetermined fundus depth position) of the fundus becomes zero. The controller 70 then moves the reference mirror 31 by a doubled amount of the calculated movement amount. This allows obtaining only the real image from the first image range G1. In this case, the variation amount of the optical-path-length matching position S corresponding to the movement amount of the reference mirror 31 may be preliminarily obtained. In view of this, the controller 70 moves the reference mirror 31 such that the deviation amount between the optical-path-length matching position S and the image detecting position becomes the predetermined amount. This allows the controller 70 to display the fundus tomographic image on a predetermined display position. A method that moves the reference mirror 31 is not limited to this method. For example, in the case where the fundus tomographic image to be obtained is determined to be a virtual image, the controller 70 may preliminarily set the movement amount (predetermined offset) of the reference mirror 31 in a direction to obtain a real image (direction to shorten the reference optical path). In this case, the controller 70 moves the reference mirror 31 by the predetermined offset if the fundus tomographic image is determined to be a virtual image.

When the fundus tomographic image to be obtained is determined to be a real image, the controller 70 may regard the position where the peak of the luminance distribution in the depth direction is detected as the image position. In this case, the controller 70 calculates the deviation amount between the optical path length adjustment position, which is preliminarily set, and the image position. The controller 70 then moves the reference mirror 31 such that the deviation amount becomes zero (see JP-A-2010-12111).

As described above, the controller 70 determines whether the fundus tomographic image, which is obtained from the first image range G1, is a real image or a virtual image. Further, the controller 70 may determine whether the first image range G1 concurrently includes the real image and the virtual image. For example, the controller 70 detects an average detecting position of the calculated maximum luminance values in respective scanning lines as an image position P1 of the fundus tomographic image. Then, the controller 70 calculates a deviation amount between the image detecting position P1 and the depth position S (lower end position of the first image range G1) of the fundus where the optical path lengths of the measurement light and the reference light match. That is, the controller 70 calculates the image position of the fundus tomographic image using the depth position S as a criterion.

The controller 70 then determines that the first image range G1 concurrently includes the real image and the virtual image when the calculated image position P1 of the fundus tomographic image is located adjacent to a lower end in the first image range G1 (for example, in a region between the lower end and a quarter of the first image range G1 from the lower end). In this case, the controller 70 moves the reference mirror 31 by a predetermined amount in a direction where the first image range G1 includes only the real image (direction to shorten the reference optical path). In this case, the movement direction and amount of the reference mirror 31 from a position where the first image range G1 concurrently includes the real image and the virtual image to a position where the first image range G1 includes only the real image may be preliminarily obtained by an experiment or a simulation and stored in the memory 72.

As described above, the first automatic optical path length adjustment, the focus adjustment, and the second automatic optical path length adjustment are performed in this order for optimization. In this embodiment, the first automatic optical path length adjustment roughly adjusts the optical path length such that the fundus tomographic image is included in the first image range G1, based on the signal intensity of the light-receiving signal output from the light-receiving element 83. On the other hand, the second automatic optical path length adjustment obtains position information in the depth direction of the fundus tomographic image, based on the light-receiving signal output from the light-receiving element 83. Then, the second automatic optical path length adjustment finely adjusts the optical path length so as to obtain the fundus tomographic image in a predetermined depth position, based on the obtained position information. The first automatic optical path length adjustment is an optical path length adjustment that allows adjusting the focus. On the other hand, the second automatic optical path length adjustment is an optical path length adjustment that adjusts the optical path length so as to optimize for photographing.

For example, the focus adjustment is performed based on luminance values of the fundus tomographic image. In view of this, it is preferred that the fundus tomographic image be included in the photographing range G of the tomographic image. In view of this, the first automatic optical path length adjustment prior to the focus adjustment roughly adjusts the optical path length so as to include the fundus tomographic image in the tomographic image. This allows a smooth focus adjustment.

As described above, the optical path length is readjusted after the focus adjustment based on the tomographic image. This allows adjusting the optical path length using the fundus tomographic image with image quality (for example, resolution and contrast) improved by the focus adjustment. This reliably guides the fundus tomographic image to a predetermined depth position (in the first image range G1 in this embodiment).

That is, in the optical path length adjustment before the focus adjustment, luminance of an image to be detected is low. This may cause an insufficient determination as to whether the image is a real image or a virtual image and an insufficient guide of the fundus tomographic image to the appropriate depth position (in the first image range G1 in this embodiment). Therefore, the optical path length (OPL) is automatically adjusted before and after the focus adjustment as described above. Then the optical path length is adjusted smoothly and stably.

This control allows appropriate adjustments of the optical path length and the focus without the dedicated optical system for photographing fundus front images such as the SLO optical system and the fundus camera optical system.

(Polarizer Adjustment)

The controller 70 drives the polarizer 33 based on the light-receiving signal output from the light-receiving element 83 after the second automatic optical path length adjustment. The controller 70 then adjusts the light polarization state.

Specifically, the controller 70 moves the polarizer 33 from the initial position to the movement start position. The initial position of the polarizer 33 is a midpoint between the first movement limiting position and the second movement limiting position. When adjusting the polarization, the movement start position of the polarizer 33 is the first movement limiting position or the second movement limiting position.

The controller 70 selects the movement start position of the polarizer 33 from the first movement limiting position or the second movement limiting position. The controller 70 then moves the polarizer 33 from the midpoint (initial position) to the selected movement start position. For example, the controller 70 selects the first movement limiting position as the movement start position, thus moving the polarizer 33 to this position. The controller 70 moves the polarizer 33 from the first movement limiting position toward the second movement limiting position. When the movement start position is the second movement limiting position, the controller 70 moves the polarizer 33 toward the first movement limiting position by predetermined increments. Then the controller 70 sequentially obtains images on a screen of the monitor 75 corresponding to the moved positions and searches a position (position where light polarization states of the measurement light and the reference light match) to receive the strong interference light.

In the search of a position where the light polarization states match one another, the controller 70 analyzes an image obtained at a position where the controller 70 stops the polarizer 33 at each of the discretely set moved positions, thus calculating the evaluation values B.

The controller 70 moves the polarizer 33 to another movement limiting position other than the movement start position in an increment of 5 degrees. The increment to move the polarizer 33 should not be construed in a limiting sense. The increment may be, for example, 10 degrees or 20 degrees. The increment may be arbitrarily set.

Here, the controller 70 detects the peak value of the evaluation values B from the calculation results of the evaluation values B corresponding to the positions of the polarizer 33. The controller 70 then moves the polarizer 33 to the position corresponding to the peak value. The polarizer adjustment is thus completed.

The optimization is then completed. This allows the examiner to observe the desired fundus portion with high sensitivity and high resolution without the dedicated optical system for photographing fundus front images such as the SLO optical system and the fundus camera optical system. The above method is also applicable to an apparatus that includes a dedicated optical system for photographing fundus front images.

Modification

A configuration that changes an optical path length difference between the optical path length of the measurement light and the optical path length of the reference light may be a configuration that changes the optical path length of the measurement light so as to adjust the optical path length difference. For example, the interference optical system 200 in FIG. 1 may include the fixed reference mirror 31 and integrally moves the relay lens 22 and the fiber end portion 39b. This allows changing the optical path length of the measurement light relative to the optical path length of the reference light.

Figure 9:
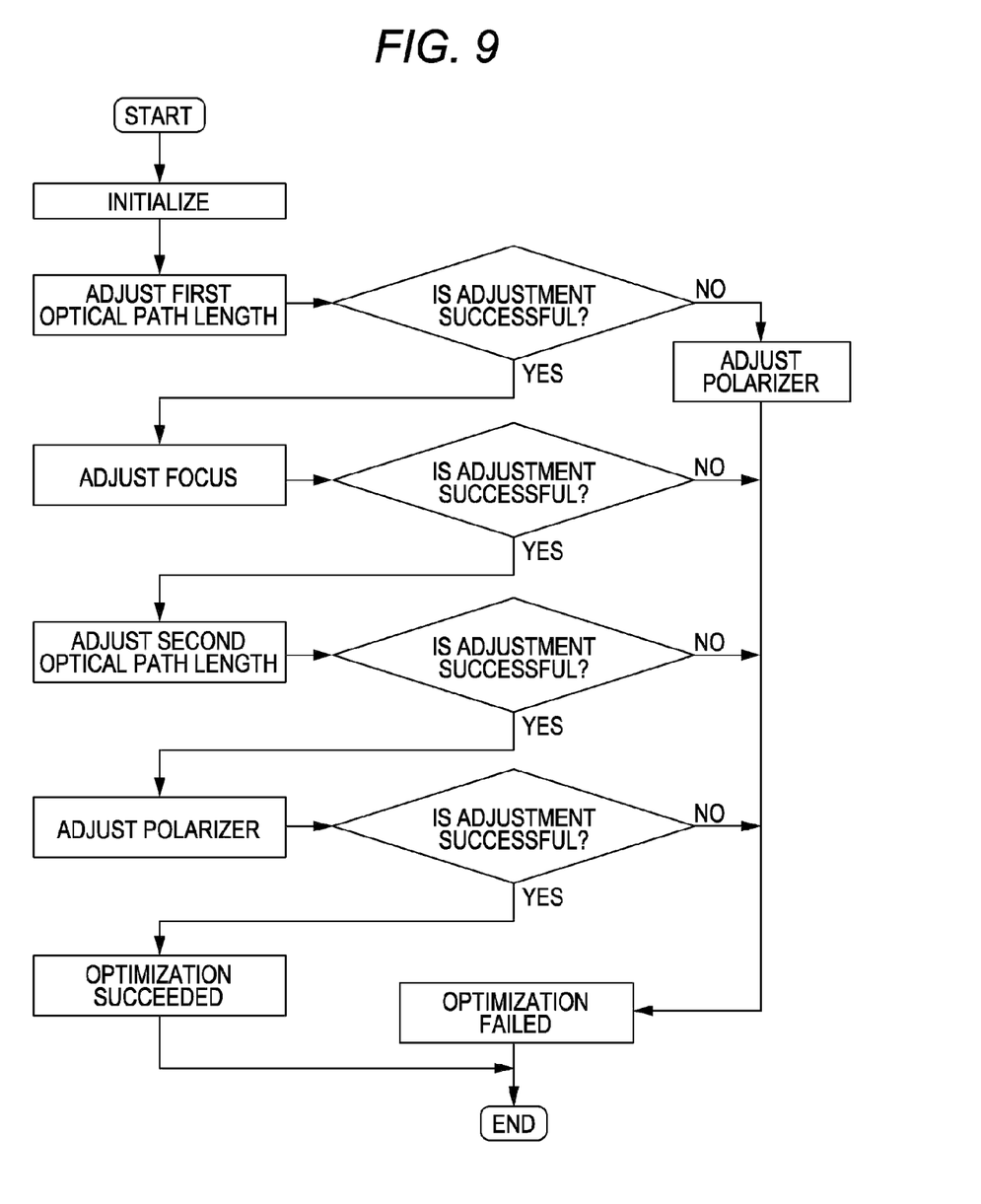
FIG. 9 is an operational flow chart of an optical tomographic image photographing apparatus according to a modification.

In the above optimization, the following adjustment is performed after completion of the previous stage of adjustment. This, however, should not be construed in a limiting sense. For example, the controller 70 may determine whether the optimization succeeds based on the luminance information of the tomographic image, and terminate the optimization based on the determination result. This is operated, for example, as shown in the flowchart of FIG. 9. The controller 70 determines whether the optimization succeeds after the first automatic optical path length adjustment. The determination may be performed, for example, based on whether a detected value (for example, the evaluation value B or the luminance value) exceeds a preliminarily set threshold value. Then, if the controller 70 determines that the optimization has failed, the controller 70 retries the optimization. The controller 70 may terminate optimization every time the optimization fails. The controller 70 may terminate optimization in the case where the optimization fails several times in a row. When optimization fails, the controller 70 may display, for example, a message of failure of the optimization on the monitor 75 so as to allow the examiner to decide whether to retry the optimization.

In a process (for example, the focus adjustment) of the optimization, when the controller 70 determines that the optimization has failed, the controller 70 may adjust a member unrelated to the process prior to the retry of the optimization. For example, the controller 70 may rotate the polarizer 33 by a predetermined degree (for example, 90 degrees) that causes the light polarization state to change when the focus adjustment has failed. Adjusting a member unrelated to the failed adjustment causes a light-receiving state of the fundus tomographic image to vary. This adjustment may allow the optimization to succeed in the retry of optimization.

The optimization in the above description includes the optical path length adjustment, the focus adjustment, and the polarizer adjustment. The adjustments included in the optimization are not limited to these configurations. For example, the optimization does not have to include the polarizer adjustment. This reduces a period for optimization. However, this leads to low sensitivity and resolution of the fundus tomographic image.

In the above description, the optimization is performed in the order of the first automatic optical path length adjustment, the focus adjustment, the second automatic optical path length adjustment, and the polarizer adjustment. This, however, should not be construed in a limiting sense. For example, the polarizer adjustment may be performed between the first automatic optical path length adjustment and the focus adjustment. The polarizer adjustment may be performed between the focus adjustment and the second automatic optical path length adjustment.

In the above description, the focus adjustment is performed between the first automatic optical path length adjustment and the second automatic optical path length adjustment. Further, one focus adjustment focuses. This, however, should not be construed in a limiting sense. For example, two focus adjustments may be performed before and after the second optical path length adjustment. In this case, the controller 70 may roughly perform the first focus adjustment insofar as the second optical path length adjustment is able to finely adjust the optical path length. The controller 70 may focus in the second focus adjustment after the second optical path length adjustment completes the fine optical path length adjustment.

Even before completion of the first automatic optical path length adjustment, a focus adjustment may be started at the point when a fundus tomographic image is obtained. That is, the first optical path length adjustment, the focus adjustment, and the second optical path length adjustment may be redundantly performed.

In the above description, the controller 70 uses the luminance distribution of the tomographic image so as to determine whether the fundus tomographic image is a real image or a virtual image. This, however, should not be construed in a limiting sense. The controller 70 may compare a cross-sectional shape of the tomographic image where a real image of the fundus tomographic image is obtained with a cross-sectional shape of the tomographic image where a virtual image of the fundus tomographic image is obtained, so as to determine whether the fundus tomographic image is a real image or a virtual image based on the comparison result. That is, the controller 70 may set a condition that allows this determination. For example, the controller 70 utilizes the state where the real image and the virtual image are mutually symmetrical with respect to a given depth position (for example, depth position S of FIG. 2). More specifically, the controller 70 extracts the retinal pigment epithelium portion from the first image range G1 of the fundus tomographic image by image processing. This image processing extracts, for example, data of luminance values that exceed a predetermined threshold value corresponding to luminance values of the retinal pigment epithelium. Then the controller 70 may determine whether the fundus tomographic image is a real image or a virtual image, based on a curved shape of the extracted retinal pigment epithelium portion. This method is also applicable to a configuration that performs dispersion correction using an optical member. This method is also applicable to a configuration that uses a combination of optical dispersion correction and dispersion correction by software.

In the above description, a photographing condition is adjusted based on a depth profile after Fourier transform. This, however, should not be construed in a limiting sense. The photographing condition may be adjusted based on the light-receiving signal output from the detector. This adjustment may use, for example, spectral data before Fourier transform.

In the above description, the apparatus includes the spectral domain OCT (OCT optical system 200) using a spectrum meter. This, however, should not be construed in a limiting sense. The apparatus may include, for example, an SS-OCT (Swept source OCT) with a variable wave-length light source.

In other words, the focus position of the focusing lens 24 is a position to focus the fundus tomographic image.

The fundus photographing apparatus according to the embodiment may be one of the following first to sixth fundus photographing apparatuses.

A first fundus photographing apparatus includes an interference optical system, an optical scanner, and a driving means. The interference optical system splits light flux emitted from a light source into a measurement light and a reference light, and then guides the measurement light flux to a fundus of an examinee's eye. The interference optical system guides the reference light to the reference light optical system, and then detects an interference state between the measurement light and the reference light reflected from the fundus with a detector. The optical scanner is disposed on an optical path of the measurement light and scans the fundus with the measurement light. The driving means drives an optical member disposed on the optical path of the measurement light or the reference light so as to adjust an optical path length difference between the measurement light and the reference light. This fundus photographing apparatus that photographs the tomographic image of the fundus based on an output signal from the detector further includes a first optical path length adjusting means, a second optical path length adjusting means, and an optical system adjusting means.

The first optical path length adjusting means controls driving of the driving means to move the optical member while moving the optical member to a position to obtain the fundus tomographic image based on the output signal output from the detector in respective positions of the optical member. The second optical path length adjusting means readjusts the position of the optical member from a position that is adjusted by the first optical path length adjusting means. The optical system adjusting means adjusts the interference optical system between operations of the first optical path length adjusting means and the second optical path length adjusting means.

A second fundus photographing apparatus according to the first fundus photographing apparatus includes a focusing optical member. The focusing optical member is disposed on an optical path of the measurement light in order to correct a diopter scale for the fundus of the examinee's eye. The optical system adjusting means is a focus adjusting means that moves the focusing optical member to a focus position on the fundus of the examinee's eye. The focus adjusting means moves the focusing optical member to a focus position on the fundus of the examinee's eye based on an output signal that is output from the detector through an optical path length adjustment by the first optical path length adjusting means. The second optical path length adjusting means readjusts the position of the optical member from the position adjusted by the first optical path length adjusting means based on the output signal output from the detector through a focus adjustment by the focus adjusting means.

A third fundus photographing apparatus according to the second fundus photographing apparatus includes a fundus observation means. The fundus observation means controls driving of the optical scanner to two-dimensionally scan the fundus with the measurement light. The fundus observation means obtains a two-dimensional moving image with respect to X-Y direction in the fundus of the examinee's eye based on an output signal from the detector.

A fourth fundus photographing apparatus according to any one of the first to third fundus photographing apparatuses includes the first optical path length adjusting means and the second optical path length adjusting means. The first optical path length adjusting means roughly adjusts the optical path length such that the fundus tomographic image is included in the tomographic image based on a signal intensity of an output signal that is output from the detector. On the other hand, the second optical path length adjusting means obtains position information in a depth direction of the fundus tomographic image based on the output signal output from the detector. The second optical path length adjusting means severely adjusts the optical path length so as to obtain the fundus tomographic image in a predetermined depth position based on the obtained position information.

A fifth fundus photographing apparatus according to any one of the first to fourth fundus photographing apparatuses includes the optical system adjusting means. The optical system adjusting means includes a polarization adjusting means. The polarization adjusting means drives a polarizing element disposed on one of the optical path of the measurement light and the optical path of the reference light, and substantially matches light polarization states of the measurement light and the reference light. The polarization adjusting means drives the polarizing element based on the output signal output from the detector after the optical path length adjustment by the second optical path length adjusting means, and adjusts the light polarization state.

A sixth fundus photographing apparatus according to any one of the first to fifth fundus photographing apparatuses includes an adjustment determination means and an optimization control means. The adjustment determination means determines whether an adjustment of optimization succeeds, based on luminance information of a tomographic image. The optimization control means terminates an adjustment of optimization based on a determination result of the adjustment determination means.

The first to sixth fundus photographing apparatuses obtain the fundus tomographic image under a photographing condition that is preferably adjusted without a dedicated optical system for photographing a fundus front image.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A fundus imaging apparatus comprising:
    an interference optical system configured to split light flux emitted from a light source into a measurement light and a reference light, the interference optical system detecting, with a detector, an interference state between the reference light and the measurement light that is reflected at a fundus of an examinee's eye;
    an optical scanner disposed on an optical path of the measurement light, the optical scanner scanning the fundus with the measurement light;
    a driver configured to drive an optical member, the optical member being disposed on the optical path of the measurement light or on an optical path of the reference light so as to adjust an optical path length difference between the measurement light and the reference light;
    a imaging unit configured to generate a tomographic image of the fundus based on an output signal from the detector;
    a first optical path length adjuster configured to obtain a light-receiving signal output from the detector corresponding to a position of the optical member while moving the optical member by controlling the driver, the first optical path length adjuster moving the optical member to a position where the fundus tomographic image is obtained, based on the light-receiving signal;
    a second optical path length adjuster configured to readjust a position of the optical member adjusted by the first optical path length adjuster; and
    an optical system adjuster configured to adjust the interference optical system between adjustments by the first optical path length adjuster and the second optical path length adjuster.

2. The fundus imaging apparatus according to claim 1, further comprising:
    a focusing optical member disposed on the optical path of the measurement light so as to correct a diopter scale for the fundus of the examinee's eye, wherein;
    the optical system adjuster includes a focus adjuster configured to move the focusing optical member to a focus position where the measurement light focuses on the fundus of the examinee's eye;
    the focus adjuster obtains the focus position based on the light-receiving signal output from the detector after the optical path length adjustment by the first optical path length adjuster, the focus adjuster moving the focusing optical member to the focus position; and
    the second optical path length adjuster readjusts the position of the optical member after a movement of the focusing optical member by the focus adjuster.

3. The fundus imaging apparatus according to claim 2, further comprising:
    a fundus observer configured to control the optical scanner to two-dimensionally scan the fundus with the measurement light, the fundus observer obtaining a two-dimensional moving image with respect to X-Y direction in the fundus of the examinee's eye based on the light-receiving signal output from the detector.

4. The fundus imaging apparatus according to claim 1, wherein
    the first optical path length adjuster adjusts the optical path length in order for a tomographic image to include the fundus tomographic image, based on a signal intensity of the light-receiving signal output from the detector; and
    the second optical path length adjuster obtains position information in a depth direction of the fundus tomographic image based on the light-receiving signal output from the detector, the second optical path length adjuster adjusting the optical path length based on the obtained position information such that the fundus tomographic image is obtained in a predetermined depth position.

5. The fundus imaging apparatus according to claim 1, wherein
the optical system adjuster includes:
a polarizing element disposed on one of the optical paths of the measurement light and the reference light; and
a polarization adjuster configured to drive the polarizing element to adjust a light polarization state of the reference light based on the light-receiving signal output from the detector, so as to substantially match the light polarization state of the reference light and a light polarization state of the measurement light after the optical path length adjustment by the second optical path length adjuster.

6. The fundus imaging apparatus according to claim 1, further comprising:
an adjustment determiner configured to determine whether the first optical path length adjuster, the second optical path length adjuster, and the optical system adjuster succeed in adjustment, based on luminance information of the fundus tomographic image; and
an adjustment terminating unit configured to terminate a subsequent adjustment when the adjustment determiner determines one of the adjustments to be failure.

7. The fundus imaging apparatus according to claim 1, wherein
the second optical path length adjuster obtains the light-receiving signal output from the detector corresponding to a position of the optical member while moving the optical member by controlling the driver, the second optical path length adjuster readjusting a position of the optical member based on the light-receiving signal.

8. A fundus imaging apparatus comprising:
a detector configured to detect an interference state between a reference light and a measurement light that is reflected at a fundus;
an optical path length adjuster configured to adjust an optical-path-length matching position where optical path lengths of the measurement light and the reference light match;
a focus adjusting member configured to adjust a focus of the measurement light; and
a controller configured to obtain a fundus tomographic image based on a light-receiving signal from the detector, wherein
the controller executes, in the following order:
a first optical path length adjustment using the optical path length adjuster to set an optical-path-length matching position to obtain the fundus tomographic image;
a focus adjustment of using the focus adjusting member to adjust the measurement light to be focused on the fundus; and
a second optical path length adjustment using the optical path length adjuster to set the optical-path-length matching position to a predetermined fundus depth position based on obtained position information from the detector.

9. The fundus imaging apparatus according to claim 8, further comprising:
a polarizing element configured to adjust at least one of a light polarization state of the measurement light and a light polarization state of the reference light, wherein the controller adjusts the polarization to substantially match the light polarization states of the reference light and the measurement light after the first optical path length adjustment.

10. A fundus imaging apparatus comprising:
an interference optical system configured to split light flux emitted from a light source into a measurement light and a reference light, the interference optical system having a detector for detecting an interference state between the reference light and the measurement light that is reflected at a fundus of an examinee's eye;
an optical scanner disposed on an optical path of the measurement light, the optical scanner scanning the fundus with the measurement light;
a driver configured to drive an optical member, the optical member being disposed on the optical path of the measurement light or on an optical path of the reference light so as to adjust an optical path length difference between the measurement light and the reference light;
an imaging unit configured to generate a tomographic image of the fundus based on an output signal from the detector;
a controller for receiving a signal output from the detector wherein said signal indicates a position of the optical member, said controller configured to activate the driver to adjust the optical member to at least a first position where a fundus tomographic image is obtained, based on, at least, the signal output from the detector;
wherein said controller is configured to execute at least a second adjustment of the position of the optical member to at least a second position; and
wherein said controller is further configured to adjust the interference optical system in response to at least adjustments of the optical member to said first position and said second position.

11. The fundus imaging apparatus according to claim 10, further comprising:
a focusing optical member disposed on the optical path of the measurement light so as to correct a diopter scale for the fundus of the examinee's eye, wherein
the controller is configured direct at least one focus driver to move the focusing optical member to a focus position where the measurement light focuses on the fundus of the examinee's eye;
the controller obtains the focus position based on the light-receiving signal output from the detector after the optical path length adjustment by the controller to a first position, the controller moving the focusing optical member to the focus position, and
the controller adapted to adjust the position of the optical member after a movement of the focusing optical member by the controller.

12. The fundus imaging apparatus according to claim 11, further comprising:
said controller further configured to control an optical scanner to two-dimensionally scan the fundus with the measurement light, said controller obtaining a two-dimensional moving image with respect to X-Y direction in the fundus of the examinee's eye based on the light-receiving signal output from the detector.

13. The fundus imaging apparatus according to claim 10, wherein
the controller adjusts the optical path length in order for a tomographic image to include the fundus tomographic image, based on a signal intensity of the light-receiving signal output from the detector; and
said controller further obtaining the position information in a depth direction of the fundus tomographic image based on the light-receiving signal output from the detector, said controller adjusting the optical path length based on the obtained position information such that the fundus tomographic image is obtained in a predetermined depth position.

14. The fundus imaging apparatus according to claim 10, further comprising:
   a polarizing element disposed on one of the optical paths of the measurement light and the reference light; and
   a polarization driver configured to drive the polarizing element to adjust a light polarization state of the reference light based on the light-receiving signal output from the detector, so as to substantially match the light polarization state of the reference light and a light polarization state of the measurement light after a second optical path length adjustment the controller.

15. The fundus imaging apparatus according to claim 10, wherein:
   said controller is further configured to determine whether the first position, the second position, and the controller adjustment of the interference optical system of the optical member to said first position and said second position succeeds in image adjustment, based on luminance information of the fundus tomographic image; and
   said controller further configured to terminate subsequent adjustments when the controller determines one of the image adjustments to be a failure.

16. The fundus imaging apparatus according to claim 10, wherein
   the controller obtains the light-receiving signal output from the detector corresponding to a position of the optical member while moving the optical member by controlling the driver, the controller further adjusting the position of the optical member based on the light-receiving signal.

17. A fundus imaging apparatus comprising:
   a detector configured to detect an interference state between a reference light and a measurement light that is reflected at a fundus;
   a controller configured to adjust an optical-path-length matching position where optical path lengths of the measurement light and the reference light match;
   said controller further configured to adjust a focus of the measurement light; and
   said controller configured to obtain a fundus tomographic image based on a light-receiving signal from the detector, wherein
   the controller executes, in the following order:
      a first optical path length adjustment to set an optical-path-length matching position to obtain the fundus tomographic image;
      a focus adjustment to adjust the measurement light to be focused on the fundus; and
      a second optical path length adjustment based on obtained position information from the detector to set the optical-path-length matching position to a predetermined fundus depth position.

18. The fundus imaging apparatus according to claim 17, further comprising:
   a polarizing element configured to adjust at least one of a light polarization state of the measurement light and a light polarization state of the reference light, wherein
   the controller adjusts the polarization to substantially match the light polarization states of the reference light and the measurement light after the first optical path length adjustment.

* * * * *